United States Patent [19]

Wirth

[11] 4,053,489
[45] Oct. 11, 1977

[54] OESTRATRIENE DIETHERS

[76] Inventor: Pierre Charles Wirth, 23, rue Francois 1er, Paris 8eme, France

[21] Appl. No.: 657,381

[22] Filed: Feb. 11, 1976

Related U.S. Application Data

[63] Continuation of Ser. No. 473,313, May 24, 1974, abandoned, which is a continuation of Ser. No. 242,138, April 7, 1972, abandoned.

[30] Foreign Application Priority Data

Apr. 21, 1971 United Kingdom ............... 10496/71

[51] Int. Cl.$^2$ .............................................. C07J 1/00
[52] U.S. Cl. ................................... 260/397.5; 424/238
[58] Field of Search ...................................... 260/397.5

[56] References Cited

U.S. PATENT DOCUMENTS 3,272,849   9/1966   Wendt et al. ..................... 260/397.5

FOREIGN PATENT DOCUMENTS 1,117,572   11/1961   Germany ......................... 260/397.5

OTHER PUBLICATIONS

C.A. 70:11874j.
C.A. 62:14764f.

Primary Examiner—Ethel G. Love
Attorney, Agent, or Firm—Haseltine, Lake & Waters

[57] ABSTRACT 3,17-Estratriene diethers, useful as anti-seborrheic and gynecological agents, is described.

7 Claims, No Drawings

OESTRATRIENE DIETHERS

This is a continuation, of application Ser. No. 473,313, filed May 24, 1974, which in turn is a continuation of application Ser. No. 242,138 filed Apr. 7, 1972, both now abandoned.

This invention is concerned with new oestratriene diethers, the preparation thereof, and pharmaceutical compositions containing them.

It has now been found, in accordance with the present invention, that certain new oestratriene diethers, as hereinafter defined, possess interesting pharmalogical activity as described more fully below.

Accordingly, the present invention provides, as new compounds, oestratriene diethers of the formula:

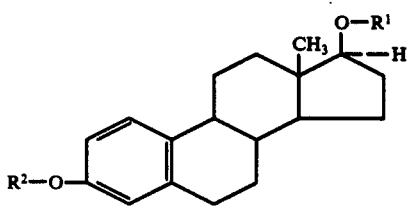

in which $R^1$ is a methyl or ethyl group and $R^2$ is an alkyl group containing from 3 to 5 carbon atoms.

The new class of oestratrienes provided in accordance with the invention comprises six members namely:

| | |
|---|---|
| 3-propoxy-17-beta-methoxy-oestra-1,3,5(10)-triene | (I) |
| 3-propoxy.17-beta-ethoxy-oestra-1,3,5 (10)-triene | (II) |
| 3-butoxy-17-beta-methoxy-oestra-1,3,5 (10)-triene | (III) |
| 3-butoxy-17-beta-ethoxy-oestra-1,3,5 (10)-triene | (IV) |
| 3-pentoxy-17-beta-methoxy-oestra-1,3,5(10)-triene | (V) |
| 3-pentoxy-17-beta-ethoxy-oestra-1,3,5 (10-triene | (VI) | and

The new compounds of the invention may be prepared from oestradiol by first preparing the 3-ether by reacting oestradiol with a $C_3$ - $C_5$ alkyl bromide and subsequently reacting the 3-ether with methyl or ethyl sulphate to introduce an ether group into the 17-position.

The following example illustrates the preparation of the first compound listed above, namely 3-propoxy-17-beta-oestra-1,3,5(10-triene.

EXAMPLE a. Preparation of oestradiol 3-propyl ether

An ethanolic solution of sodium ethoxide is prepared by reacting 3 grams of sodium with 300 ml of absolute ethanol. 30 grams of oestradiol are dissolved in the resultant solution and there are then added thereto, with stirring, 30 ml of n-propyl bromide. Reaction is continued for 3 hours with stirring at 60° C and then the reaction mixture is concentrated under vacuum at 30° C to about 50 ml. The residue is taken up in 500 ml of benzene and then washed twice with 250 ml of a 0.25 normal solution of sodium hydroxide and then with distilled water to neutrality. The solution is then dried over sodium sulphate and concentrated to give 32 grams of crude product (yield 93%), which on recrystallization from 100 ml of methanol gives 31 grams (yield 89%) of pure product melting at 100° - 101° C.

b. Preparation of 3-propoxy-17-beta-methoxy-oestra-1,3,5 (10)-triene

40 Grams of the 3-propyl-ether obtained in (a) above is dissolved in 400 ml of anhydrous dimethyl sulphoxide. Several crystals of triphenylmethane are added to the solution (as a coloured indicator) followed by freshly prepared dimethyl sulphinyl carbanion (sodium) until a permanent red colour is obtained. There is then added about 50% excess dimethyl sulphinyl carbanion (sodium). The reaction mixture is allowed to stand for about 15 minutes at ambient temperature and is then cooled on an ice bath.

40 ml of redistilled methyl sulphate are then slowly added to the mixture which is then stirred for 15 minutes at room temperature.

The excess methyl sulphate is then destroyed by the addition of about 2 liters of 2N sodium hydroxide and the mixture stirred for about 2 hours. The pH of the reaction mixture must be alkaline at the end of the operation. The reaction mixture is extracted with benzene and the benzene fractions are washed with distilled water to neutrality. The benzene extracts are then dried over sodium sulphate and concentrated under vacuum at 33° C to give 42 grams of crude product which on repeated recrystallisation from ethanol gives a pure white product in a yield of 78% melting at 66° - 67° C. (Reichert). The purity of the end product is controlled by gas phase and thin layer chromotography.

It will be clear that other compounds in accordance with the invention may be prepared in a similar manner by replacing the propyl bromide or methyl sulphate reactants with equivalent amounts of pentyl or butyl bromide or ethyl sulphate. It is thus possible to obtain the six compounds referred to above having the following characteristics:

| Compound No. | Melting Point (° C) | $[\alpha]_{25}^D$ in ethanol |
|---|---|---|
| I | 66–67 | 0.97 |
| II | — | — |
| III | 56.5–57.5 | 1.08 |
| IV | — | — |
| V | 54–55 | — |
| VI | — | — |

As stated above, the new compounds of the invention possess interesting pharmacological properties and, in particular, when applied to the skin and/or the mucous membranes, they exhibit a marked local trophic and anti-seborrheic activity whilst being practically devoid of any oestrogenic activity.

Thus, in the Allen and Doisy tests, total oestrus of castrated rats is obtained by the injection in oily solution (0.2 ml) of 120±10 micrograms of 3-propoxy-17-beta-methoxy-oestratriene, 210±10 micrograms of 3-butoxy-17-beta-methoxy oestratriene and 310±10 micrograms of 3-pentoxy-17-beta-methoxy oestratriene. In general, the oestrogenic activity decreases with increase in the length of the side chain at the 3-position and, thus, 3-hexoxy 17-beta-methoxy-oestratriene is inactive in the above tests even at a dose of 500 micrograms. When administered cutaneously in the above test, the above four compounds have active dosages 2–4 micrograms, 2–3 micrograms, 20–30 micrograms and 100 micrograms, respectively. When administered as oily injections, the first of the above compounds has an active dosage of 70±100 micrograms and the last of the compounds is still inactive even when administered at a level of 300 micrograms.

Replacement of the 17-methoxy group by a 17-ethoxy group does not markedly affect the biological activity of the new compounds.

The batch of castrated Whistar rats used in the above tests have a sensitivity to 17-beta-oestrdiol of 0.6±0.05 micrograms and one can deduce from this test that 3-propoxy-17-beta-methoxy-oestratriene has an activity of 200 times less than that of 17-beta-oestradiol and the butoxy compound has an oestrogenic activity of about one three-hundredth of that of 17-beta-oestradiol.

The following table indicates the oestrogenic activity of 17-beta-oestradiol and various compounds in accordance with the invention as determined by uterotrophic tests on prepubic mice 21–23 days old.

| Oestrogen | Dose required to double the weight of the uterus. (micrograms) |
|---|---|
| 17-Beta-Oestradiol | 0.01 |
| 3-propoxy-17-beta-methoxy-oestratriene | 2 |
| 3-butoxy-17-beta-methoxy-oestratriene | 2 |
| 3-pentoxy-17-beta-methoxy-oestratriene | 2 |

The oestrogens are administered as 5% aqueous ethanolic solutions on 3 consecutive days and the animals are sacrificed 72 hours afterwards. The uterotrophic activity of the three compounds in accordance with the invention is about 200 times less than that of 17-beta oestradiol. In contrast to what is found in the tests on castrated rats, the uterotrophic activity of the compounds in accordance with the invention does not appear to depend on the length of the chain of the substituent in position-3.

Further, the ethers in accordance with the invention are fairly weak oestrogens since like oestriol their uterotrophic activity levels out when the weight of the uterus has been increased by 2–2.5 times in contrast to the case of the strong oestrogens, such as oestradiol, in which the uterus weight may increase by 6 times. Thus, in conclusion, the double etherification of 17-beta-oestradiol at the 3- and 17-positions gives rise to products having a very weak oestrogenic activity in animals and none in man when administered in much larger doses than the therapeutically effective doses.

The second experimental fact which characterises the diethers in accordance with the invention is their relatively strong activity in the Allen and Doisy test when they are administered in 95° alcohol to Whistar rats. By this route oestrus is obtained in the castrated rat at a dosage of 1.5±0.5 micrograms for 3-propoxy-17-beta-methoxy-oestratriene and for the same dose for 3-butoxy-17-methoxy-oestratriene whilst oestradiol, when applied by the same route, is active at a level of 0.6 micrograms.

The ratio "degree of activity by cutaneous application": "degree of activity by subcutaneous injection in oily solution" for oestradiol is about unity, for 3-propoxy-17-beta-methoxy-oestratriene is 80 and for 3-butoxy-17-beta-methoxy-oestratriene is 150. If the chain length of the 3-substituent is increased the ratio decreases, falling to approximately 10 for 3-hexoxy-17-beta-methoxy-oestradiene.

This unexpected behaviour of the oestradiol diethers may be explained by the presence in the dermal tissue of rats of an enzyme which is capable of hydrolysing oestradiol ethers, but which is not present in the other tissues of the animal. This hypothesis explains the very low activity of the diethers in the Allen and Doisy test when they are administered by injection as compared with the relatively high activity when the products are administered to the skin.

Another unexpected interesting phenomenon (characterising the oestradiol diethers) resides in the fact that if the dosage of 3-propoxy-17-beta-methoxy-oestratriene or 3-butoxy-17-beta-methoxy-oestratriene is raised from 1 to 5 micrograms, no appreciable increase in the length of oestrus is found and this remains less than 24 hours. This is markedly different from the behaviour of oestradiol which when applied in ethanolic solution in a dosage of 5 micrograms to the skin of the animal produces an oestrus lasting an average of 5 days.

The above results may be explained by the fact that, because of the saturation of the enzyme, the amount of 17-beta-oestradiol liberated in the skin by hydrolysis of the diethers, is relatively constant for doses of 1 to 5 milligrams; the freed hormone achieving a relatively important concentration in the skin but the concentration being insufficient to have any important general effect.

In other words, by etherifying the 17-hydroxyl group with a methyl or ethyl radical and etherifying the 3-hydroxyl group with a propyl or butyl group, there is obtained a compound having a relatively powerful oestrogenic activity in situ (intradermic) but which is insignificant with regard to the whole body. This general effect is however sufficient for, in the castrated rat, a fraction of a microgram of oestradiol leads to vaginal oestrus. The double etherification of 17-beta-oestradiol permits one to "focus" or localise the activity of 17-beta-oestradiol in the epithelial tissue and it is this principle which forms the base of the present invention and from which the therapeutic uses of the compounds arise.

Thus, with particular reference to pharmalogical tests carried out with 3-propoxy-17-beta-methoxy-oestradiol (compound No. 1), the following results can be given.

I. Gonado-inhibiting activity

Compound No. 1, when administered by injection, is a little less than 80 times active as a gonado-inhibitor than is ethinyl-oestradiol when administered by injection, and compound No. 1, when administered by the oral route, is about 20 times less active as a gonado-inhibitor than is ethinyl-oestradiol when administered by the same route.

The method used consists in evaluating the degree of inhibition of the weight of the testicles in the young rat (and of the androgyenic receptors) as a result of the administration of a compound possibly having gonado-inhibiting activity. The results are expressed as $ED_{50}$ namely that dose which produces in the animal under treatment a 50% reduction in weight of the testicles, as compared with the testicles of control animals.

The compounds under test are administered daily over a period of 14 days, by either the subcutaneous or oral route, all the compounds used being administered in the same volume using the same excipient.

The gonado-inhibiting $ED_{50}$ of the compound under test is compared with the same $ED_{50}$ for a reference substance, for example ethinyl-oestradiol. The following results are obtained:

Administration by subcutaneously route

The $ED_{50}$ of compound No. 1 is 19 micrograms/animal/day.

The $ED_{50}$ of ethinyl-oestradiol is 0.25 micrograms-/animal/day.

Administration by oral route

The $ED_{50}$ of compound No. 1 is 20 micrograms-/animal/day.

The $ED_{50}$ of ethinyl-oestradiol is 1.2 micrograms-/animal/day.

II. Anti-Seborrheic activity

It is known that androgens give rise to certain modifications of various cutaneous parameters (for example the development and secretive activity of the sebaceous glands or the proliferation of the epidermic epithelium) whilst castration or estrogens have an effect on the same parameters but in the opposite way.

These principles form the base of a test method which is considered the best and most reliable of all those which may be used to test the anti-seborrheic activity of a given substance (Ebling F.J. -J.embryol. Exp. Morph. 1957, 5, 1 : 74–82 and numberous other subsequent publications).

The test animals used are castrated male rats which are allowed to rest for 3 to 4 weeks and then implanted, on day 0, with a pellet containing 12 mg of testosterone. Random lots of the animals are made up. On day 8, the animals are bathed in a 10% solution of sodium lauryl sulphate then dried in a current of warm air. They are again bathed on day 0 and after drying, a specimen of hair is removed, weighed and placed in ethyl ether. At day 17, a second specimen of hair is taken.

At time 0 on day 17, all the animals receive an intraperitoneal injection of colchicine. Then, at time 5 hours on the same day, each animal is sacrificed and a sample of the skin is immediately taken. At the same time, the seminal vesicles and the ventral prostates are also taken.

From day 0 to day 17 all of the animals, other than the control animals, receive a daily treatment. The following table gives the results obtained for 3 lots of control animals and 6 lots of treated animals.

| Weight of ventral prostate (mg) | Weight of seminal vesicules (mg) | | * = doses/animal/day x = p < 0.05 xx = p < 0.01 xxx = p < 0.001 | SEBUM mg/g/d | Number of mitoses in glands | Number of mitoses in epithelium | Number of nuclei of spumous cells | Thickness of epithelium |
|---|---|---|---|---|---|---|---|---|
| 386.9 | xxx 480.1 | CONTROLS | NORMAL | 0.73 | 33.6 | 76.1 | 133.9 | 13.5 |
| 6.2 | xxx 5.9 | | CASTRATED | xx 0.51 | x 12.3 | 44.0 | xxx 94.9 | xx 11.5 |
| 164 | 215.5 | | CASTRATED+ TESTOSTERONE | 0.88 | 26.6 | 67.6 | 129.5 | 13.6 |
| xx 159.2 | 166.8 | CASTRATED | +E₂ 10μg*SC | x 0.64 | 31.2 | 65.0 | xx 101.6 | xxx 9.8 |
| x 133.4 | 230.5 | + | +E₂ 30μg*SC | xx 0.515 | 27.4 | xx 31.7 | xxx 78.6 | xxx 7.3 |
| 156.1 | 242.2 | TESTOSTERONE | +I 30μg*SC | x 0.59 | 22.2 | 53.5 | xxx 74.4 | xxx 8.9 |
| 160 | 247.9 | | +I 90μg*SC | xxx 0.43 | 22.0 | 42.0 | xxx 75.4 | xxx 8.7 |
| 177.3 | xxx 317.3 | | +I 270μg*SC | xxx 0.34 | x 14.1 | xx 29.9 | xxx 61.9 | xxx 5.8 |
| 158.6 | 210 | | +I 30μg*P.C. | 0.70ns | 17.2ns | x 32.9 | 111.5ns | xxx 10.6 |

| Weight of ventral prostaic (mg) | Weight of seminal vesicules (mg) | | * = doses/animal/day x = p < 0.05 xx = p < 0.01 xxx = p < 0.001 | LIPIDS (SEBUM) mg/g/day | Number of mitoses gl/2cm | $\frac{LIPIDS}{MITOSES} \times 10^3$ |
|---|---|---|---|---|---|---|
| 386.9 | xxx 480.1 | CONTROLS | NORMAL | 0.73 | 33.6 | 21.7 |
| 6.2 | xxx 5.9 | | CASTRATED | 0.51 | 12.3 | 41.5 |
| 164 | 215.5 | | CASTRATED+ TESTOSTERONE | 0.88 | 26.6 | 23.1 |
| 159.2 | xx 166.8 | CASTRATED | +E₂ 10μg*SC | 0.64 | 31.2 | 20.5 |
| x 133.4 | 230.5 | + | +E₂ 30μg*SC | 0.515 | 27.4 | 18.8 |
| 156.1 | 242.2 | TESTOSTERONE | +I 30μg*SC | 0.59 | 22.2 | 26.6 |
| 160 | 247.9 | | +I 90μg*SC | 0.43 | 22.0 | 19.6 |
| 177.3 | xxx 317.3 | | +I 270μg*SC | 0.34 | 14.1 | 24.1 |
| 158.6 | 210 | | +I 30μg*P.C. | 0.70 | 17.2 | 40.7 |

$E_2$ = 12 beta-estradiol;
S.C. = sub-cutaneous;
P.C. = percutaneous (cutaneous application of the product in alcoholic solution)

The following facts may be deduced from the above table:

a. Sebum decreases with castration and is restored by the Testosterone implant which does not, however, restore the androgenic receptors;

decreases with $E_2$, 27% for a dosage of 10 micrograms and 41% for a dosage of 30 micrograms, this latter does neutralising the response of the androgenic receptors with regard to the pellet;

decreases with compound No. 1 (.S.C.) in a comparable manner and markedly progressively with the dosage, but only a little by the P.C. route.

b. The Number of Mitoses in the Cells of the Sebaceous Glands decreases with castrating and is restores with Testosterone;

does not decrease with $E_2$ upto a dosage of 30 micrograms/day (S.C. but does decrease with 270 micrograms of compound No. I (S.C.).

c. Thelial cells decrease with castration, but rise with Testosterone;

decrease with $E_2$, in proportion to the dose.

e. Thickness of the Epithelium decreases with castration and is restored with Testosterone;

decreases with $E_2$ in proportion to the dose;

decreases with Compound I.P.C. less from 30 micrograms per day and S.C. much more.

f. Relationship Between Sebum and the Number of Mitoses in the Glands decreases with $E_2$ due solely to the reduction, in proportion to the dose, of sebum;

decreases with compound No. I, S.C. for the same reason with compound No. 1,P.C., the number of mitoses decreases but not the amount of sebum; in these last two cases the ratio increases.

It may thus be concluded that the behaviour of compound No. 1 (3-propoxy-17-beta-methoxy-oestradiol) was qualitatively analogous to that of $E_2$, but is quantitatively superior (i.e. gives a greater effect at the same dose). Further, compound No. 1, when administered by the SC route has an estrogenic effect less 5% of that of $E_2$, which again illustrates the superiority of compound No. 1 over $E_2$.

These facts are confirmed in man in that the two above mentioned diethers do not possess any feminishing activity when they are applied to the skin, in an oil-in-water, water-in-oil or hydroalcoholic excipients, or in oily solution, at daily doses exceeding 20 mg even after daily treatment for six months. The same is true when the products are sprayed on to the nasal or buccal mucous membranes in solution in perhydrosqualene, are applied to the scalp in ethanolic or hydro-ethanolic solution, or are introduced in the vagina in the form of a cream or gynecological capsules.

To sum up, the two above diethers and the corresponding compounds having a 17-beta methoxy group have a powerful trophic action on the skin, scalp and mucous membranes and have an important antiseborrheic effect. Thus, the principal therapeutic uses of the diethers may be summarised as follows.

1. Skin conditions

Acne, seborrhea, pigment, dehydration and all other skin conditions arising from ageing.

2. Gynecological conditions

The diethers have a powerful trophic effect on the vaginal mucous membranes without acting on the secretion of the cervical mucous. These properties may be used in the treatment of different forms of vulvitis and vaginitis; secondary infections, to stimulate healing of surgical or obstetric wounds; in cases of vaginal discomfort or dyspareunia due to oral contraception or climate, etc. In such treatment, the diethers may be used in conjunction with antifungal and/or bactericidal and/or antiparastical medicaments.

3. Ear, Nose and Throat conditions

The diethers may be used in the treatment of infections (in association with an antibiotic), atrophy of the nasal mucous membranes, pseudo-allergic conditions of the upper respiratory tract, bad breath, stomatitis and anginitis.

4. Seborrhea of the scalp, with or without loss of hair

The diethers act on the suppleness and quality of the hair and not only againt seborrheic hypersecretion.

In accordance with another embodiment of the invention, there is provided a pharmaceutical composition comprising a diethr in accordance with the invention, together with a pharmaceutical carrier or diluent.

The pharmaceutical compositions of the invention will take various forms, depending upon their intended use. Thus, for treatment of skin conditions, the compositions may be in the form of a cream, pomade of gel which may be an emulsion in a continuous oily or aqueous phase, and will be generally compounded with suitable conventional excipients; or in a form for oral administration such as tablets or capsules containing the diether dissolved in olive oil.

The following is an example of a suitable composition.

| Example A | |
|---|---|
| Oestradiol diether | 2 g |
| Perhydrosqualene | 30 g |
| Beeswax | 10 g |
| Vaseline | 20 g |
| Sorbitan sequioleate | 3 g |
| Sodium borate | 0.65 g |
| Sodium methyl para-hydroxybenzoate | 0.1 g |
| Sodium propyl para-hydroxybenzoate | 0.05 g |

For gynaecological conditions, the compositions may be, for example, in the form of a dry or glycerinic ovule, a gynaecological capsule, a foam, pressurised composition (aerosol), dressing or liquid for instillation. The following is an example of a suitable composition.

| Example B | |
|---|---|
| Oestradiol diether | 2 g |
| Fatty acid triglycerides | 40 g |
| Mono and diglycerides of palmitic and stearic acids | 10 g |
| Soya lecithin | 5 g |
| Glycerine mono- and dioleate | 13 g |

For ear, nose and throat conditions, the composition may be in the form of a solution for instillation or in aerosol form in an aqueous or oily vehicle. An example of such a composition is given below.

| Example C | | |
|---|---|---|
| Oestradiol diether | 1 g | |
| Perhydrosqualene | 100 g | |
| Eucalyptol | 0.5 g | |
| Freon 12 | 9.5 g | |
| | 9.5 | for pressurised container |

For treatment of the scalp, the compositions may be applied as alcoholic, aqueous/alcholic, glyceroalcoholic or lypo alcoholic lotions, or in the forms of various emulsions. In other words, the compositions may comprise conventional excipients known to be acceptable for application to the scalp.

Examples of suitable compositions are given below:

| Example D | |
|---|---|
| Oestradiol diether | 1 g |
| Oxyethylene ester of branched chain fatty acid | 30 g |
| Water | 20 g |

-continued

| | |
|---|---|
| Ethanol (90°) | 49 g |
| Example E | |
| Oestradiol diether | 1 g |
| Diisopropyl adipate | 20 g |
| Isopropyl alcohol | 60 g |
| Glycerol | 10 g |
| Water | 9 g |
| Example F | |
| Oestradiol diether | 1 g |
| Branched chain fatty acid ester | 10 g |
| Ethanol (90°) | |

In all the above Examples, the concentration of the oestradiol diether may vary from 0.5 to 5% it being noted that the preferred diether is compound No. 1.

A number of clinical trials have been carried out on compound No. 1 (under the code number J-015) and the following is a resume of the results of these trials.

A. Dermatology a. A first investigator carried out tests on 61 patients of both sexes and all ages, each presenting signs of dermo-epidermic ageing and seborrheic diathesis. This investigator used a cream containing 1 to 2% of J-015 in daily or two-daily applications.

The results were judged on the basis of the responses noted for 86 pathological symptoms and are summarised in the following table.

It is convenient to note that despite the dosages used and the very prolonged period of treatment in most cases, none of the 53 women or young girls treated showed any trouble with their menstrual cycle and none of the 30 men treated had suffered troubling of the libido or other oestrogenic (gynecomastia) or anti-androgenic symptoms.

The following table summarises the results obtained in these experiments.

| Results | Very good | Good | Fairly good | Mediocre |
|---|---|---|---|---|
| Number of cases | 21 | 13 | 9 | 13 |
| Results | None | Fairly good or good but not re-examined | | |
| Number of cases | 17 | 3 | | |

Thus the overall results were favourable in 46 cases (61%) of which 31% were without doubt excellent (44.7%); whilst they were unfavourable in 30 cases (29.4%) of which 17 (22%) were absolutely nil results.

It should be noted that in all these cases the illness had evolved over a period of months and, more often, over a period of several years.

| | Number of cases | Very good | Good | Medium | Failure |
|---|---|---|---|---|---|
| SEBORRHEA | 46 | 5 | 18 | 12 | 11 |
| 35/46 favourable = 76.08% | 33F 13M | 5F 0M | 12F 6M | 8F 4M | 8F 3M |
| 23/46 very good and good = 50% | | | | | |
| ACNE | 26 | 1 (F) | 8 | 10 | 7 |
| 16/26 favourable (61.5%) | 22F 4M | | 6F 2M | 8F 2M | 7F 0M |
| 9/26 very good and good (34.6%) | | | | | |
| KERATOSES PRE-EPITHELIOMAT.; EPITHELIOMAS PAGET. | 7 | 0 | 1 (M) | 4 | 2 |
| | 4F 3M | | | 3F 1M | 1M 1M |
| SEBORRHEIC WARTS | 4 (F) | 1 | 0 | 2 | 1 |
| VULVIC ATROAN + KRAUROSIS | 3 | 0 | 0 | 3 | 0 |
| TOTAL | 86 | 7 | 27 | 31 | 21 |

F = female
M = male b. A second investigator administered the same type of cream to 83 subjects of both sexes aged from 13 to 47 years, all showing seborrheic symptoms with or without acne.

In this case also, treatment was daily and the investigator was able to calculate the dose of active product effectively received each day by his treatments; the doses varied from 3.3 to 26 mg per day, the great majority of patients (102 out of 128) having received from 7 to 13 mg per day.

Treatment lasted for:
less than 6 weeks in the case of 13 patients;
between 2 and 3½ months in the case of 13 patients;
between 2 and 3½ months in the case of 25 patients;
between 4 and 6½ months in the case of 28 patients; and
between 7 and 12 months in the case of 17 patients.

| INDICATIONS | Very Good or Good | Medium | None | Total |
|---|---|---|---|---|
| Trophic Vaginitis | 28 | | | 28 |
| Non-monopausic Dyspareunic | 3 | 1 | | 4 |
| Healing after electro-coagulation | 8 | | 1 | 9 |
| Healing after episiotomia | 6 | | | 6 |
| Other gynaecological conditions | 3 | | | 3 |
| TOTAL | 48 | 1 | 1 | 50 |
| Infective Vaginitis | 3 | 3 | 6 | 12 |

A good number of the patients treated in this trial had previously received other treatments, generally reputed to be efficacious (for example anti-conception agents, antibiotics, small doses of seric gonadotrophine etc.). In 15 cases which had previously failed to respond to such known therapeutic agents, J-015 cream was used 19 times and gave five successes, of which three were outstanding, and was unsuccessful 14 times. In 5 cases which had suffered relapse after previous treatment, J-015 cream gave two complete successes. In 11 cases in which incomplete results had been obtained with previous treatment, J-015 cream gave 8 cures.

B. Gynaecology

15 Patients were treated in order to investigate the trophic effects of J-015 on the vulvo-vaginal epithelium and also to define the degree of eventual estrogenic activity of this steroid when applied to a sensitive receptor.

The medicament was administered in the form of an identical cream to that used in the dermatological tests referred to above, in the form of gynaecological gelatine capsules containing an emulsion containing 5 mg of active ingredient per capsule (formula B) or 10 mg per capsule (formula A).

With regard to the oestrogenic effects these were practically nil as evidenced by the non-appearance of mucous cervical secretion and insignificant modification of the cyto-hormonal content of the vaginal epiphelium.

One observation in particular illustrates the disassociation exhibited by the steroid under consideration between its trophic effects (which are excellent) and its hormonal effects which are only sketchy and do not progress either with the doses employed or with prolonged treatment. This observation concerns a case of trophic vaginitis wherein the retraction was such that the vagina permitted the passage of only one finger, and where there was also a secondary infection. After four months of application of the dermatological cream, once per day for the first two months and then once every two days, the vagina allowed the passage of two fingers and sexual intercourse was possible. The infection spontaneously disappeared without other treatment. Further, only 5% of superficial cells were found at the pycnotic nucleus after the four months treatment and despite the improvement in the condition (in place of 0 before treatment).

Finally, in the case of women having menstrual activity no disturbance of the menstrual cycle was noted after gynecological treatment with J-015.

What we claim is:

1. A compound of the formula

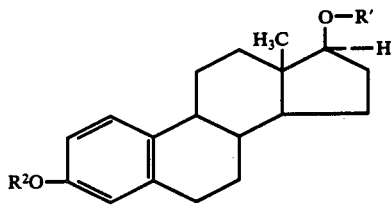

wherein $R^1$ is a methyl or ethyl group and $R^2$ is an alkyl group having 3 to 5 carbon atoms.

2. A compound as claimed in claim 1 which is 3-propoxy-17-beta-methoxy-oestra-1,3,5(10)-triene.

3. A compound as claimed in claim 1 which is 3-propoxy-17-beta-ethoxy-oestra-1,3,5(10)-triene.

4. A compound as claimed in claim 1 which is 3-butoxy-17-beta-methoxy-oestra-1,3,5(10)-triene.

5. A compound as claimed in claim 1 which is 3-butoxy-17-beta-ethoxy-oestra-1,3,5(10 )-triene.

6. A compound as claimed in claim 1 which is 3-pentoxy-17-beta-methoxy-oestra-1,3,5(10)-triene.

7. A compound as claimed in claim 1 which is 3-pentoxy-17-beta-ethoxy-oestra-1,3,5(10)-triene.

* * * * *